US010729827B2

(12) United States Patent
Jessop et al.

(10) Patent No.: US 10,729,827 B2
(45) Date of Patent: Aug. 4, 2020

(54) SYRINGE FILLING DEVICE FOR FAT TRANSFER

(71) Applicant: LifeCell Corporation, Branchburg, NJ (US)

(72) Inventors: Israel Jessop, Annandale, NJ (US); Aaron Barere, Hoboken, NJ (US); Kai-Roy Wang, Jersey City, NJ (US); Mark Hayzlett, Flemington, NJ (US)

(73) Assignee: LifeCell Corporation, Madison, NJ (US)

( * ) Notice: Subject to any disclaimer, the term of this patent is extended or adjusted under 35 U.S.C. 154(b) by 681 days.

(21) Appl. No.: 15/386,450

(22) Filed: Dec. 21, 2016

(65) Prior Publication Data

US 2017/0173227 A1 Jun. 22, 2017

Related U.S. Application Data

(60) Provisional application No. 62/270,789, filed on Dec. 22, 2015.

(51) Int. Cl.
*A61M 1/00* (2006.01)
*A61B 17/00* (2006.01)
*A61M 5/178* (2006.01)

(52) U.S. Cl.
CPC . *A61M 1/0094* (2014.02); *A61B 2017/00792* (2013.01); *A61B 2217/005* (2013.01); *A61M 5/1782* (2013.01); *A61M 2202/08* (2013.01)

(58) Field of Classification Search
CPC ............ A61M 2202/08; A61M 1/0094; A61M 5/1782; A61B 2017/00792
See application file for complete search history.

(56) References Cited

U.S. PATENT DOCUMENTS

| 3,791,524 A | 2/1974 | Cho |
| 4,681,571 A | 7/1987 | Nehring |
| 4,753,634 A | 6/1988 | Johnson |
| 5,209,732 A | 5/1993 | Lampropoulos et al. |
| 5,301,685 A | 4/1994 | Guirguis |
| 5,330,914 A | 7/1994 | Uhlen et al. |
| 5,336,616 A | 8/1994 | Livesey et al. |
| 5,372,945 A | 12/1994 | Alchas et al. |
| 5,409,833 A | 4/1995 | Hu et al. |
| 5,610,074 A | 3/1997 | Beritashvili et al. |

(Continued)

FOREIGN PATENT DOCUMENTS

| EP | 0512769 A2 | 11/1992 |
| JP | 2009189282 A | 8/2009 |

(Continued)

OTHER PUBLICATIONS

Coleman et al., Fat grafting to the breast revisited: safety and efficacy. Plast Reconstr Surg. Mar. 2007;119(3):775-85.

(Continued)

*Primary Examiner* — Adam Marcetich
*Assistant Examiner* — Jessica R Arble
(74) *Attorney, Agent, or Firm* — McCarter & English, LLP

(57) ABSTRACT

The present disclosure provides systems and methods for transfer of tissue or other materials such as adipose tissue. The systems and methods can include a vessel and a syringe to facilitate transfer of tissue between one or more vessels and tissue implantation devices.

14 Claims, 13 Drawing Sheets

(56) References Cited

U.S. PATENT DOCUMENTS

| | | | |
|---|---|---|---|
| 5,785,640 A | 7/1998 | Kresch et al. | |
| 5,786,207 A | 7/1998 | Katz et al. | |
| D401,336 S | 11/1998 | Muller et al. | |
| 5,901,717 A | 5/1999 | Dunn et al. | |
| 5,968,356 A | 10/1999 | Morsiani et al. | |
| D424,194 S | 5/2000 | Holdaway et al. | |
| 6,200,606 B1 | 3/2001 | Peterson et al. | |
| 6,258,054 B1 | 7/2001 | Mozsary et al. | |
| 6,261,549 B1 | 7/2001 | Fernandez et al. | |
| 6,478,966 B2 | 11/2002 | Zhou et al. | |
| 6,544,788 B2 | 4/2003 | Singh | |
| 6,733,537 B1 | 5/2004 | Fields et al. | |
| D492,995 S | 7/2004 | Rue et al. | |
| 6,852,533 B1 | 2/2005 | Rafii et al. | |
| 7,011,755 B2* | 3/2006 | Zuk, Jr. | B01D 29/05 210/416.1 |
| 7,172,572 B2 | 2/2007 | Diamond et al. | |
| 7,328,549 B2 | 2/2008 | Kinney et al. | |
| 7,361,368 B2 | 4/2008 | Claude et al. | |
| 7,390,484 B2 | 6/2008 | Fraser et al. | |
| D575,393 S | 8/2008 | Stephens | |
| 7,429,488 B2 | 9/2008 | Fraser et al. | |
| 7,473,420 B2 | 1/2009 | Fraser et al. | |
| 7,501,115 B2 | 3/2009 | Fraser et al. | |
| 7,514,075 B2 | 4/2009 | Hedrick et al. | |
| 7,585,670 B2 | 9/2009 | Hedrick et al. | |
| 7,588,732 B2 | 9/2009 | Buss | |
| 7,595,043 B2 | 9/2009 | Hedrick et al. | |
| 7,651,684 B2 | 1/2010 | Hedrick et al. | |
| 7,687,059 B2 | 3/2010 | Fraser et al. | |
| 7,708,152 B2 | 5/2010 | Dorian et al. | |
| 7,732,190 B2 | 6/2010 | Michal et al. | |
| 7,744,820 B2 | 6/2010 | Togawa et al. | |
| 7,749,741 B2 | 7/2010 | Bullen et al. | |
| 7,780,649 B2 | 8/2010 | Shippert | |
| 7,780,860 B2 | 8/2010 | Higgins et al. | |
| 7,789,872 B2 | 9/2010 | Shippert | |
| 7,794,449 B2 | 9/2010 | Shippert | |
| 7,887,795 B2 | 2/2011 | Fraser et al. | |
| 7,901,672 B2 | 3/2011 | Fraser et al. | |
| 8,062,286 B2 | 11/2011 | Shippert | |
| 8,100,874 B1 | 1/2012 | Jordan et al. | |
| 8,293,532 B2 | 10/2012 | Moynahan | |
| 8,333,740 B2 | 12/2012 | Shippert | |
| 8,366,694 B1 | 2/2013 | Jordan | |
| D679,011 S | 3/2013 | Kitayama et al. | |
| 8,409,860 B2 | 4/2013 | Moynahan | |
| D683,851 S | 6/2013 | Greenhalgh | |
| D687,549 S | 8/2013 | Johnson et al. | |
| D692,559 S | 10/2013 | Scheibel et al. | |
| 8,622,997 B2 | 1/2014 | Shippert | |
| 8,632,498 B2 | 1/2014 | Rimsa et al. | |
| 8,887,770 B1 | 11/2014 | Shippert | |
| 2001/0030152 A1 | 10/2001 | Wright et al. | |
| 2002/0188280 A1 | 12/2002 | Nguyen et al. | |
| 2004/0005246 A1 | 1/2004 | Efthimiadis et al. | |
| 2004/0097867 A1 | 5/2004 | Fraser et al. | |
| 2005/0084961 A1 | 4/2005 | Hedrick et al. | |
| 2006/0051865 A1 | 3/2006 | Higgins et al. | |
| 2006/0184119 A1 | 8/2006 | Remde et al. | |
| 2006/0224144 A1 | 10/2006 | Lee | |
| 2007/0106208 A1 | 5/2007 | Uber et al. | |
| 2007/0225665 A1 | 9/2007 | Perez-Cruet et al. | |
| 2007/0248575 A1 | 10/2007 | Connor et al. | |
| 2008/0014181 A1 | 1/2008 | Ariff et al. | |
| 2008/0050275 A1 | 2/2008 | Bischof et al. | |
| 2009/0042267 A1 | 2/2009 | Park | |
| 2009/0181104 A1 | 7/2009 | Rigotti et al. | |
| 2009/0287190 A1 | 11/2009 | Shippert | |
| 2009/0299328 A1 | 12/2009 | Mudd et al. | |
| 2010/0174162 A1 | 7/2010 | Gough et al. | |
| 2010/0268189 A1 | 10/2010 | Byrnes et al. | |
| 2010/0285521 A1 | 11/2010 | Vossman et al. | |
| 2010/0285588 A1 | 11/2010 | Stubbers et al. | |
| 2011/0009822 A1 | 1/2011 | Nielsen | |
| 2011/0117650 A1 | 5/2011 | Riordan | |
| 2011/0198353 A1 | 8/2011 | Tsao | |
| 2012/0003733 A1 | 1/2012 | Gueneron | |
| 2012/0214659 A1 | 8/2012 | Do et al. | |
| 2013/0131635 A1 | 5/2013 | Rimsa et al. | |
| 2013/0150825 A1 | 6/2013 | Rimsa et al. | |
| 2013/0158515 A1 | 6/2013 | Austen, Jr. | |
| 2013/0324966 A1 | 12/2013 | Park et al. | |
| 2014/0276592 A1* | 9/2014 | Mottola | A61M 5/31505 604/506 |
| 2014/0291234 A1* | 10/2014 | Chi | B01D 29/085 210/406 |
| 2014/0363891 A1* | 12/2014 | Llull | C12M 45/09 435/378 |

FOREIGN PATENT DOCUMENTS

| | | |
|---|---|---|
| JP | 201112581 A | 1/2011 |
| WO | 2009/055610 A1 | 4/2009 |
| WO | 2011/052946 A2 | 5/2011 |
| WO | 2012/006587 A2 | 1/2012 |
| WO | 2012/019103 A2 | 2/2012 |
| WO | 2012/083412 A1 | 6/2012 |
| WO | 2012/109603 A1 | 8/2012 |
| WO | 2012/139593 A2 | 10/2012 |
| WO | 2013/090579 A1 | 6/2013 |
| WO | 2013/106655 A1 | 7/2013 |
| WO | 2014/033209 A1 | 3/2014 |
| WO | 2014/070525 A1 | 5/2014 |

OTHER PUBLICATIONS

Delay et al., Fat injection to the breast: technique, results, and indications based on 880 procedures over 10 years. Aesthet Surg J. Sep.-Oct. 2009;29(5):360-76.

Pakhomov et al., Hydraulically coupled microejection technique for precise local solution delivery in tissues. J Neurosci Methods. Sep. 15, 2006;155(2):231-40.

Smith et al., Autologous human fat grafting: effect of harvesting and preparation techniques on adipocyte graft survival. Plast Reconstr Surg. May 2006;117(6):1836-44.

Ting et al., A new technique to assist epidural needle placement: fiberoptic-guided insertion using two wavelengths. Anesthesiology. May 2010;112(5):1128-35.

Yoshimura et al., Cell-assisted lipotransfer for cosmetic breast augmentation: supportive use of adipose-derived stem/ stromal cells. Aesthetic Plast Surg. Jan. 2008;32(1):48-55.

Invitation to Pay Additional Fees for Application No. PCT/US2016/058171, dated Mar. 2, 2017.

International Search Report and Written Opinion for Application No. PCT/US2016/067991, dated Apr. 21, 2017.

* cited by examiner

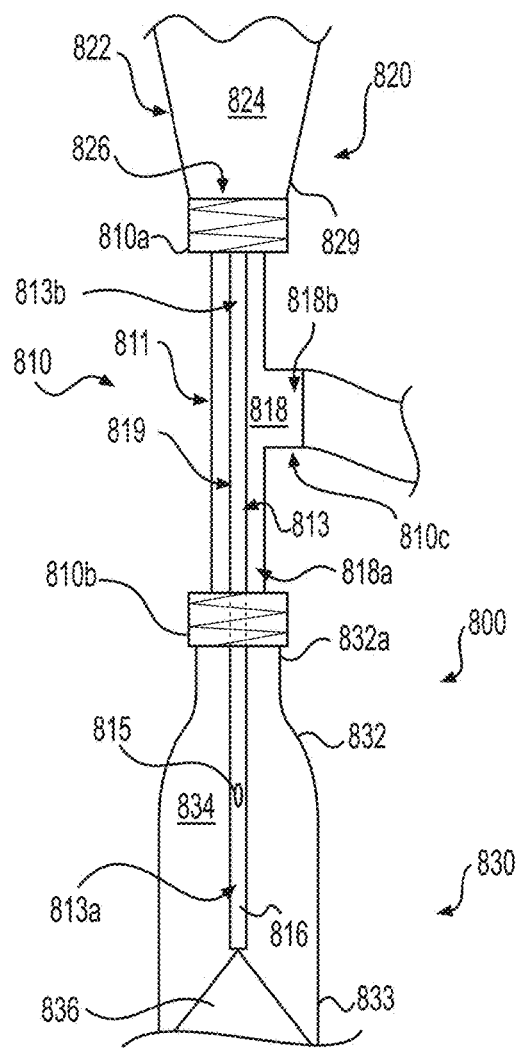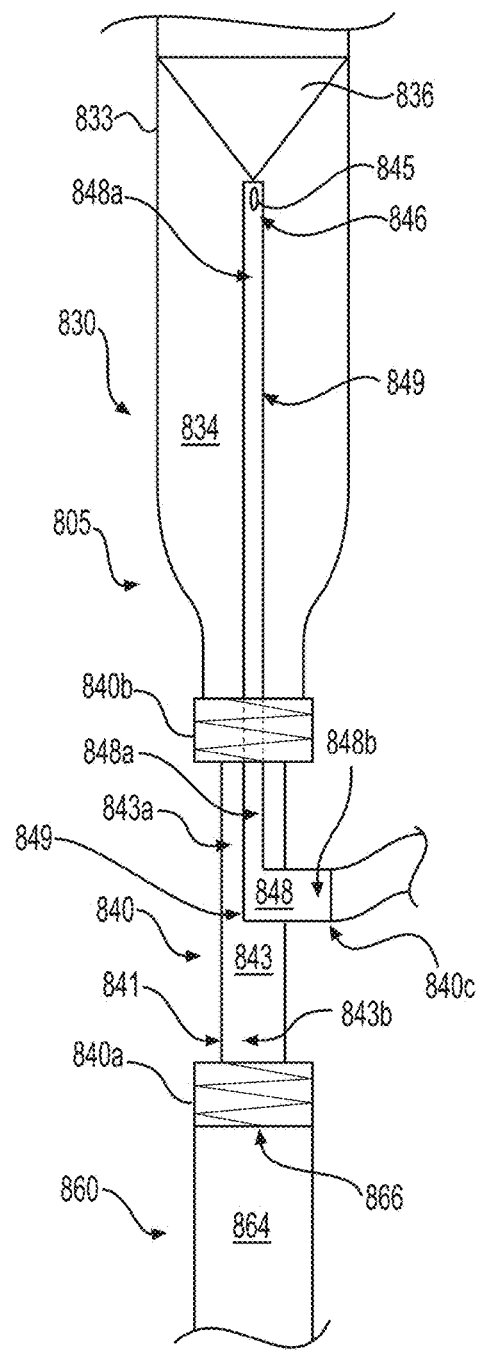
FIG. 8A
FIG. 8B

SYRINGE FILLING DEVICE FOR FAT TRANSFER

This application claims priority to U.S. Provisional Patent Application No. 62/270,789, filed Dec. 22, 2015, the entire contents of which is incorporated herein by reference.

The present disclosure relates to surgical instruments and methods including instruments and methods for transfer of tissue such as adipose tissue.

Autologous fat grafting has become increasingly common and has numerous clinical applications such as facial contouring, breast reconstruction and/or augmentation, and other aesthetic or reconstructive procedures. In addition, autologous fat grafting has been found to have relatively low donor-site morbidity compared with other surgical options.

In some cases, however, autologous fat grafting provides somewhat unpredictable outcomes. For example, the amount of adipose cell viability after implantation is variable, and this issue can result in less than optimal outcomes and/or require multiple or revision procedures.

Adipocyte viability can be affected by a number of factors including aspiration pressure, injection pressure, and sheer stress. If done improperly, the loading and unloading of cells from syringes and other vessels can result in damage to the cells and reduce overall cell viability after implantation. To mitigate these effects, the user must exert careful control over pressures and sheer stresses when loading and unloading cells. This control can be achieved by introducing a level of automation and repeatability in cell transfer.

Adipose tissue transfer generally requires one or more steps wherein adipose tissue is passed between tissue collection or delivery devices. These steps can be time-consuming. In addition, the transfer steps, including loading of delivery vessels or syringes, can cause a reduction in cell viability if undesirably large forces (e.g., shear forces) are placed on tissues during the process.

The present disclosure provides devices and methods for improved tissue transfer, including devices and methods for transferring adipose tissue. The devices and methods allow controlled loading of adipose delivery devices, and can reduce operative times, while controlling tissue transfer processes to increase or control the consistency of cell viability during tissue transfer.

A tissue transfer system is provided according to various embodiments described herein. The tissue transfer system includes a material holding or processing vessel. The material holding or processing vessel includes an exterior wall surrounding an interior volume for holding tissue, an outlet in fluid communication with the interior volume, and an exterior fluid passage having an opening disposed proximate an opening of the outlet. The tissue transfer system also includes a syringe. The syringe includes a syringe body having an interior volume and a syringe tip comprising a peripheral wall having a distal opening forming a first passage in fluid communication with the interior volume. The syringe tip is adapted to be mated with the outlet of the material holding or processing vessel such that the opening of the outlet is in fluid communication with the first passage of the syringe tip and the exterior fluid passage of the material holding or processing vessel is in fluid communication with the interior volume of the syringe body.

A tissue transfer vessel is provided according to various embodiments described herein. The tissue transfer vessel includes an exterior wall surrounding an interior volume for holding a tissue and an elongated lumen extending from the exterior wall to an outlet. The tissue transfer vessel also includes an exterior fluid passage having a proximal opening, a lumen, and a distal opening. The proximal opening, lumen, and distal opening are external to the interior volume, and the distal opening is located proximate an opening of the outlet.

A method of transferring tissue or other material to a syringe is provided according to various embodiments described herein. The method includes selecting a material holding or processing vessel having an outlet and an exterior fluid passage and containing a tissue or other material to be transferred. The method includes mating an end of a syringe to the outlet of the vessel to place the interior of the syringe body and the interior of the vessel into fluid communication and to place the exterior fluid passage and the interior of the vessel into fluid communication. The method includes attaching a negative pressure source to the exterior fluid passage. The method includes engaging the negative pressure source to draw the tissue or other material from the vessel through the outlet and into the syringe body.

A tissue transfer adapter is provided according to various embodiments described herein. The tissue transfer adapter includes an adapter body comprising an outer wall and a first end, a second end, and a third end. The tissue transfer adapter also includes an elongated body passing from the first end and extending through the adapter body and past an opening in the second end to a distal tip. The elongated body contains a lumen extending therethrough. The tissue transfer adapter also includes a fluid passage contained within the outer wall and fluidly coupling the opening of the second end with an opening in the third end. The first end of the adapter body is configured to be mated with a container or fluid conduit such that an interior volume of the container or fluid conduit is in fluid communication with the lumen of the elongated body such that upon application of suction to the opening in the third end, a material contained within the container or fluid conduit will be drawn through at least a portion of the lumen of the elongated body and out of the elongated body.

A tissue transfer adapter is provided according to various embodiments described herein. The tissue transfer adapter includes an adapter body comprising an outer wall and a first end, a second end, and a third end. The adapter body comprises an opening in each of the first end and the second end. The tissue transfer adapter includes a fluid passage contained within the outer wall and fluidly coupling the opening of the first end with the opening in the second end. The tissue transfer adapter includes an elongated body in fluid communication with an opening in the third end that extends from the third end through the adapter body and past the opening in the second end to a distal tip. The elongated body contains a lumen extending therethrough to a distal opening. The first end of the adapter body is configured to be mated with a container or fluid conduit such that an interior volume of the container or fluid conduit is in fluid communication with the fluid passage such that upon application of suction to an opening in the third end, a material contained within the container or fluid conduit will be drawn into the opening in the first end and out of the opening in the second end.

A method of transferring tissue using the tissue transfer adapter is provided according to various embodiments described herein. The method includes providing a tissue transfer adapter as described above. The method includes coupling a syringe to the opening in the second end. The method includes coupling a material holding or processing vessel to the opening in the first end. The method includes attaching a source of negative pressure to the opening in the third end. The method includes applying a negative pressure such that a tissue exits the material holding or processing vessel and enters an interior volume of the syringe.

A tissue transfer device is provided according to various embodiments described herein. The tissue transfer device includes a material holding or processing vessel that includes an exterior wall surrounding an interior volume for holding tissue. The exterior wall includes an adapter body comprising an outer wall and a first end, a second end, and a third end. The adapter body comprises an opening in each of the first end and the second end. The exterior wall includes a fluid passage contained within the outer wall and fluidly coupling the opening of the first end with the opening in the second end. The exterior wall includes an elongated body in fluid communication with an opening in the third end that extends from the third end through the adapter body and past the opening in the second end to a distal tip. The elongated body contains a lumen extending therethrough to a distal opening. The first end of the adapter body is mated with the material holding or processing vessel such that an interior volume of the material holding or processing vessel is in fluid communication with the fluid passage such that upon application of suction to an opening in the third end, a material contained within the material holding or processing vessel will be drawn into the opening in the first end and out of the opening in the second end.

A method of transferring tissue or other material to a syringe using the tissue transfer device is provided according to various embodiments described herein. The method includes selecting a material holding or processing vessel as described above and containing tissue or other material to be transferred. The method includes mating a proximal portion of a syringe to a second opening of the tissue transfer adapter of the vessel to place the interior of the syringe body and the interior of the vessel into fluid communication through an elongated body. The method includes attaching a negative pressure source to a third opening of the tissue transfer adapter. The method includes engaging the negative pressure source to draw the tissue or other material from the vessel through the tissue transfer adapter and into the syringe body.

BRIEF DESCRIPTION OF THE DRAWINGS

FIG. 8A illustrates a cross-sectional view of an adapter to fill syringes with tissue, according to various embodiments.

FIG. 8B illustrates a cross-sectional view of an adapter to fill syringes with tissue, according to various embodiments.

DESCRIPTION OF CERTAIN EXEMPLARY EMBODIMENTS

Figure 1A:
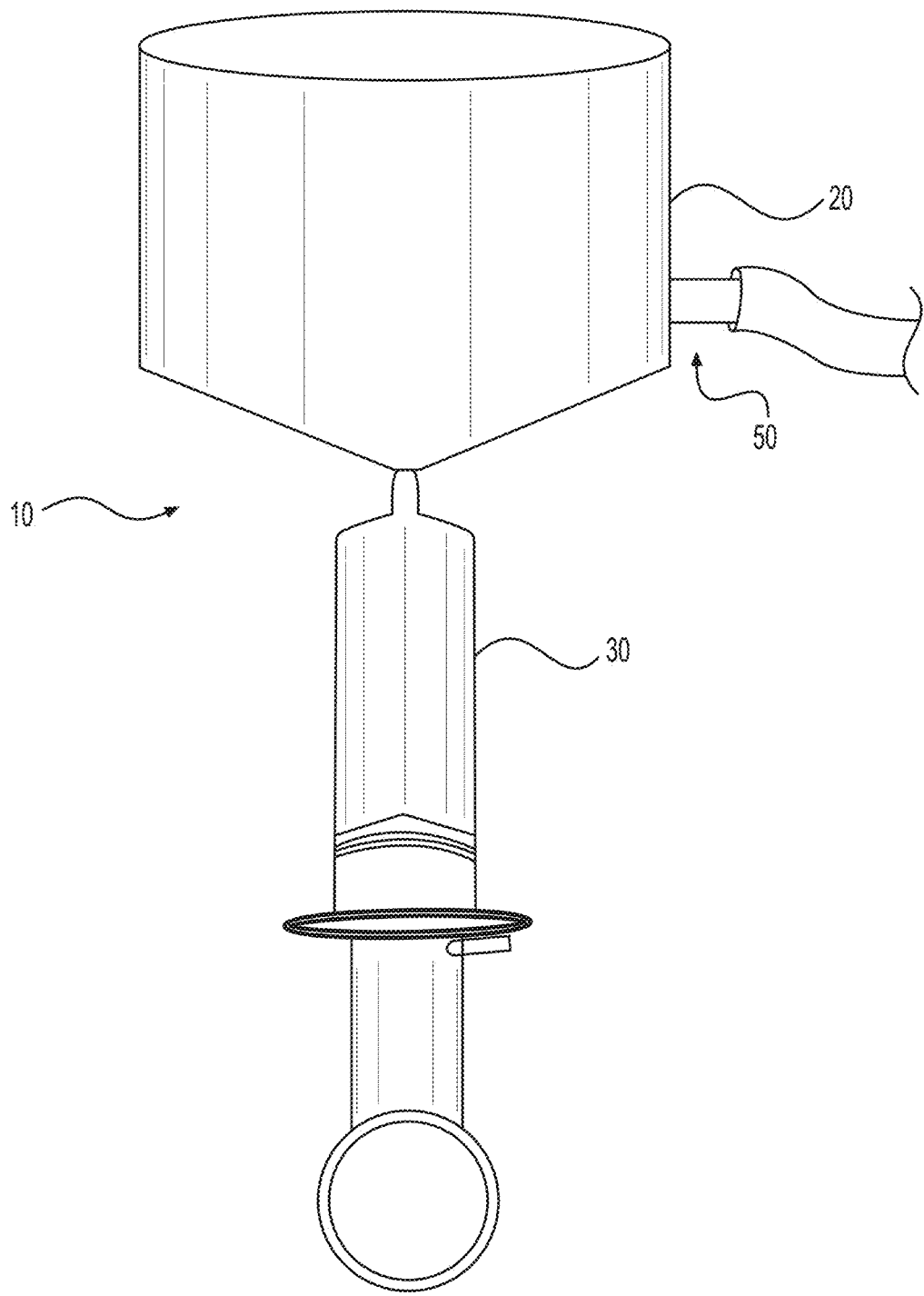
FIG. 1A illustrates a perspective view of a system for transferring tissue, according to various embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms such as "included" and "includes", is not limiting. In this application, the use of the word "exterior" is not limited to strictly external locations but is also extended to mean "not in fluid communication with".

The use of the word "syringe" is not limited to any industry standard and includes any of a variety of receptacles in different shapes and sizes. Any range described herein will be understood to include the endpoints and all values between the endpoints. In this application, "gravitationally higher than" refers to an object further from the Earth's surface than another object while "gravitationally lower than" refers to an object closer to the Earth's surface than another object.

The section headings used herein are for organizational purposes only and are not to be construed as limiting the subject matter described. All documents, or portions of documents, cited in this application including but not limited to patents, patent applications, articles, books, and treatises are hereby expressly incorporated by reference in their entirety for any purpose.

Various human and animal tissues can be used to produce products for treating patients. For example, various tissue products have been produced for regeneration, repair, augmentation, reinforcement, and/or treatment of human tissues that have been damaged or lost due to various diseases and/or structural damage (e.g., from trauma, surgery, atrophy, and/or long-term wear and degeneration). Fat grafting, including autologous fat grafting, can be useful for a variety of clinical applications including facial fillers, breast augmentation, buttock augmentation/sculpting, augmentation of other tissue sites, correction of lumpectomy defects, cranialfacial defect correction, and correction of lipoplasty defects (divots).

Grafting of various tissues, however, can be unpredictable and can sometimes result in variable outcomes, multiple procedures, and/or revision surgeries. Although the precise reasons for graft variability are not always known, there is evidence that the viability of grafted cells, including grafted adipose tissues, is affected by surgical techniques such as the amount of pressure and/or shear stress applied to the grafts as they are transferred among vessels and syringes during aspiration and re-injection.

Control of surgical technique during tissue manipulation can be complex. For example, it may be difficult for clinicians to determine the pressure and/or shear applied to grafts during a particular transfer procedure. This can be true for a variety of reasons. For example, the pressure and shear stress exerted on a sample can relate to a number of variables including properties of the particular vessels and injection devices used (e.g., syringe and needle/cannula size, transfer rate, vessel outlet size, vessel withdrawal rate, vessel and injection device material properties [e.g., friction properties], tissue viscosity, clogging of cannulas, and backpressure from a host site) or other mechanical properties. See, e.g., U.S. patent application Ser. No. 14/682,342, titled "Injection Sensor with Feedback Mechanism," to Barere et al., which describes devices for controlling shear and/or other adipose injection variable, and is herein incorporated by reference. Accordingly, the present disclosure provides devices and methods to facilitate control of surgical techniques to improve graft outcomes.

In addition, loading of injection devices or otherwise transferring tissue prior to implantation or during processing can be time consuming. Accordingly, the present disclosure provides devices and methods that assist in loading/unloading of tissue transfer devices, thereby reducing operative time. In some embodiments, the systems, devices, and methods can be used to transfer adipose tissues or other implantable materials (e.g., injectable or implantable gels, pastes, or putties).

As used herein, "adipose tissue" refers to adipose tissue obtained by any means including, for example, liposuction and/or tumescent liposuction. In addition, the adipose tissue may be substantially intact or may be altered by, for example, washing with saline, antimicrobials, detergents, or other agents; the addition of therapeutic agents such an analgesics, antimicrobials, and anti-inflammatories; the removal of some cells or acellular components; or disruption or alteration by the collection process itself including, for example, during liposuction or tumescent liposuction. The adipose tissue can be autologous tissue, allogeneic tissue, or xenogenic tissue (e.g., porcine tissue).

In one embodiment, a tissue transfer system includes a vessel and a syringe, wherein the vessel has an exterior fluid passage through which a negative pressure can be applied. As discussed in detail below, the exterior fluid passage can be in fluid communication with the interior of the syringe and the vessel and can be configured to facilitate transfer of tissue from the vessel into the syringe. The vessel can be constructed in such a way as to limit the ability of the tissue material to enter the exterior fluid passage, thereby preventing clogging of the passage.

Figure 1B:
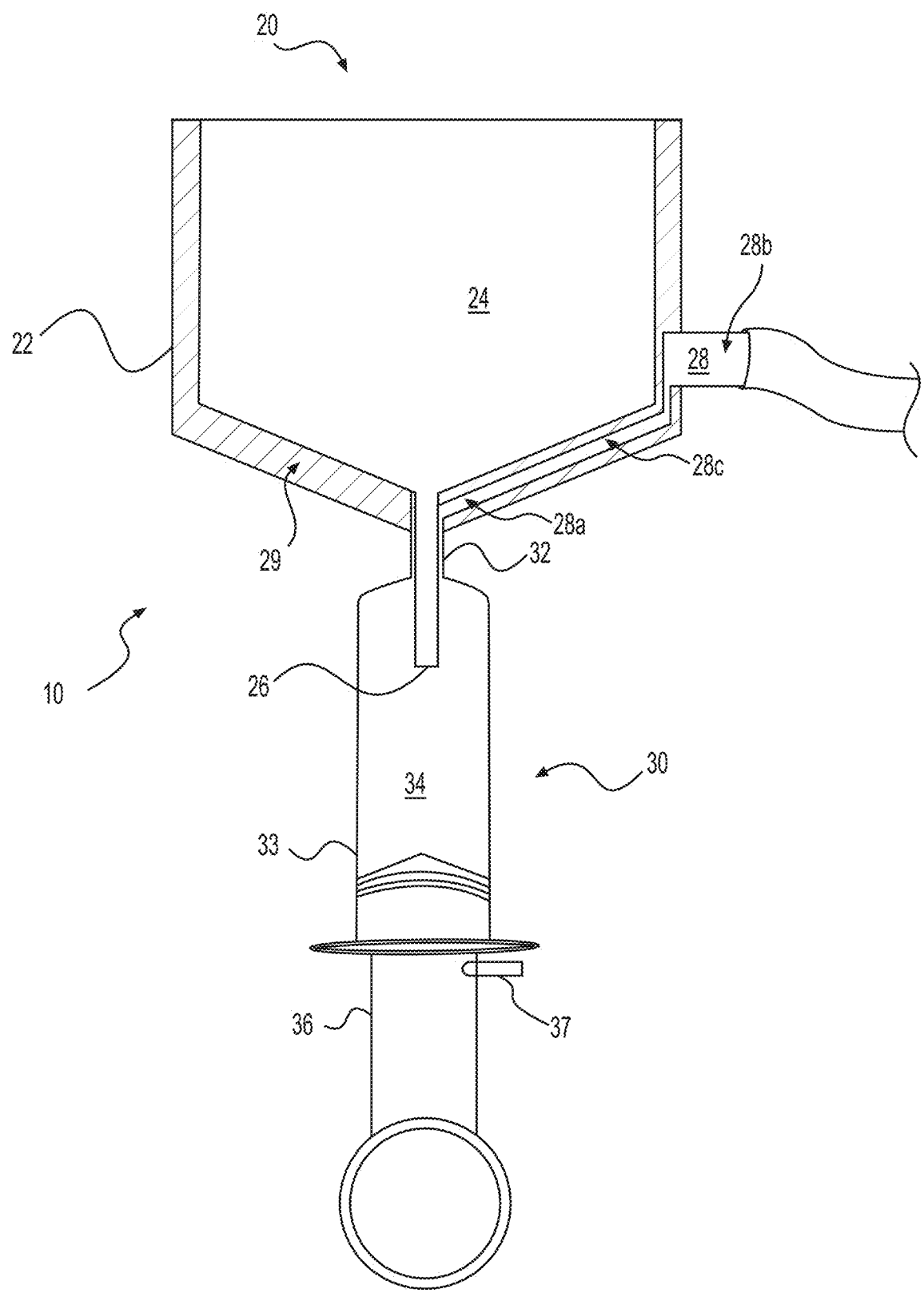
FIG. 1B illustrates a cross-sectional view of the system shown in FIG. 1A.
Figure 2:
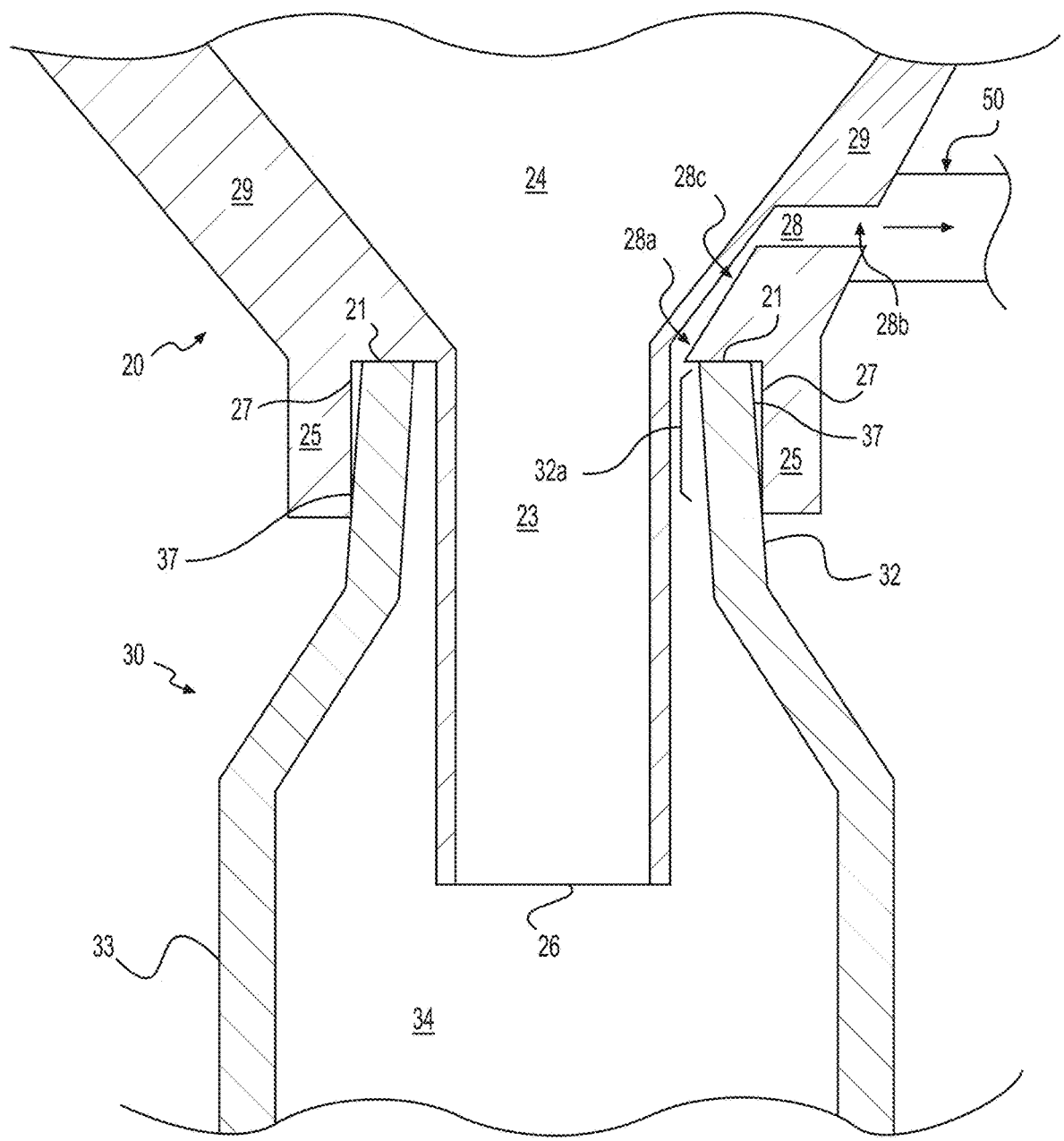
FIG. 2 illustrates an enlarged view of a portion of the system shown in FIGS. 1A and 1B.

FIGS. 1A and 1B illustrate perspective and cross-sectional views, respectively, of a system 10 for transferring tissue, according to various embodiments; and FIG. 2 illustrates a magnified cross-sectional view of a portion of the system 10.

The system 10 can include a material holding or processing vessel 20 and a syringe 30. As discussed further below, the material holding or processing vessel 20 can include an exterior wall 22 surrounding an interior volume 24 and an outlet 26 in fluid communication with the interior volume 24. In addition, the material holding or processing vessel can also include an exterior fluid passage 28 that includes a lumen 28c and has one end proximal 28a to an opening of the outlet 26. In exemplary embodiments, the end 28a of the exterior fluid passage 28 is placed gravitationally higher than the opening of the outlet 26 to minimize aspiration of tissue into the exterior fluid passage during a transfer operation. The syringe can also include a syringe tip 32 and a syringe body 33 having an interior volume 34. The syringe tip 32 can be adapted to mate with the vessel outlet 26. When the syringe 30 and vessel 20 are mated and a negative pressure is applied to the distal end 28b of the external fluid passage 28, tissue material contained within the vessel 20 will be pulled from the interior volume 24 of the vessel 20 into the interior volume 34 of the syringe body 33.

The material holding or processing vessel 20 can be formed of a variety of materials and have a variety of shapes. In some embodiments, the vessel 20 has a bottom portion 29 that is predominantly conical in nature and that terminates at an outlet 26. The outlet 26 can have a variety of suitable configurations, e.g., with a circular, elliptical, or other polygonal cross-sectional shape.

In some embodiments, the material holding or processing vessel 20 can further include an elongated lumen 23 that extends from the exterior wall 22 to the outlet 26. The length of the lumen 23 may be selected such that the outlet 26 at the syringe tip 32 extends into the syringe body 33 when the syringe 30 and vessel 20 are mated. When the outlet 26 is extended into the syringe body 33 (and particularly extended gravitationally lower than the inlet 28a), material contained within the vessel 20 such as, for example, adipose tissue can be transferred to the interior volume 34 of the syringe body 33 but will not easily pass into the exterior fluid passage 28. As a result, the tissue is prevented from blocking or clogging the lumen 28c of the exterior fluid passage 28 during operation.

The term "syringe" is meant, according to the present application, to refer generally to any tissue holder or container that may be used to receive and transfer tissue. It will be apparent in view of the present disclosure that the syringe 30 can take the form of a range of devices in accordance with various embodiments and that the characteristics of the syringe device can vary depending upon application-specific requirements. According to various embodiments, the syringe 30 contains a syringe body 33, a syringe tip 32, and a plunger 36 that seals the interior volume of the syringe. In alternative embodiments, the syringe 30 may be a further material holding or processing vessel or simply a tissue holding system where tissue is collected and retained for later use. According to various embodiments, the syringe 30 may be a tissue holding container suitable for cold- or cryo-storage, or the syringe 30 may be a device similar to a bulb or bladder that can be compressed to expel the tissue after loading.

The material holding or processing vessel 20 may further include a mating surface 21 that makes contact with an end 32a of the syringe tip 32. The contact between the mating surface 21 and the end 32a of the syringe tip 32 can produce a seal to prevent leakage of material outside of the vessel 20 and syringe 30 during transfer. This seal can be achieved, for example, by coating the mating surface 21 with a pliant, air-tight and/or water-tight material, by placing an O-ring at the mating surface, or simply through the pressure applied to mate the vessel 20 and syringe 30.

In some embodiments, the material holding or processing vessel 20 further includes a ridge 25 that facilitates mating between the syringe 30 and the vessel 20. The ridge 25 concentrically surrounds the outlet 26 in exemplary embodiments. The ridge 25 can include an interior surface 27 that is configured to mate with an exterior lateral surface 37 of the syringe tip 32. The ridge 25 can help guide the syringe tip 32 into a proper position to mate with the outlet 26 of the vessel 20. In certain embodiments, the mating surface 21 may act as a positioning element by halting the insertion of the syringe tip 32 at a given point.

In some embodiments, the distal end 28b of the exterior fluid passage 28 can include an adapter 50 to facilitate connection of a source of negative pressure. For example, the adapter 50 could be a plastic through-port, a luer-type connector, a threaded connector, a swage fitting, or a pressure-fit connector. In various embodiments, the negative pressure source could be a standalone vacuum pump or in-house vacuum provided in an operating room or related facility. In accordance with various embodiments, the proximal end 28a of the exterior fluid passage 28 may be located near the outlet 26 of the material holding or processing vessel 20. In some embodiments, the proximal end 28a of the exterior fluid passage 28 can be located gravitationally higher than the outlet 26 of the material holding or processing vessel 20. In embodiments containing an elongated lumen 23, the proximal end 28a of the exterior fluid passage 28 may be located adjacent to the elongated lumen 23 of the material holding or processing vessel 20 such that the exterior fluid passage 28 and elongated lumen 23 are only in fluid communication through the outlet 26.

The syringe 30 may further include a plunger 36 that is adapted to move longitudinally within the syringe body 33. The plunger 36 seals the interior volume 34 of the syringe 30 to allow a negative pressure source connected to the distal end 28b of the exterior fluid passage 28 to create negative pressure within the interior volume of the syringe 34. When the syringe 30 is unmated from the vessel 20, the plunger 36 can then be used to force material out of the syringe's interior volume 34 through the syringe tip 32. In some embodiments, the syringe 30 further includes a locking mechanism 37 that can secure the plunger 36 in a selected longitudinal position. The locking mechanism 37 may be used to hold the plunger 36 at particular positions to limit the size of the interior volume 34. In addition, the plunger 36 may be locked so that it does not move as a negative pressure is applied to the interior volume 34 via the exterior fluid passage 28.

Figure 3A:
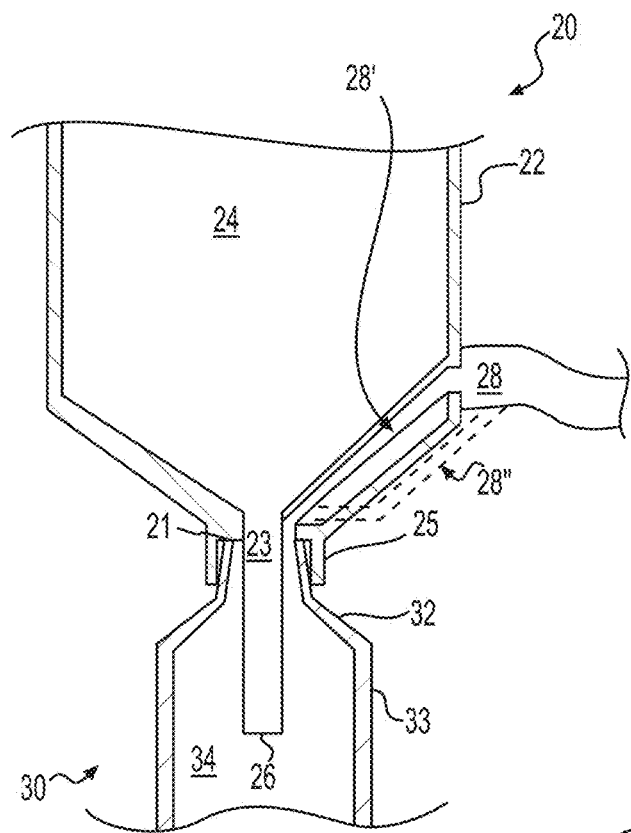
FIG. 3A illustrates a cross-sectional view of a portion of a system for transferring tissue, according to various embodiments.

FIG. 2 illustrates one configuration for the device 10. However, a number of variations can be included. For example, as illustrated in FIG. 3A, the exterior fluid passage 28 can have alternative locations and configurations. For example, the exterior fluid passage 28 may consist of a lumen 28' that is at least partially interior to the exterior wall 22 of the material holding or processing vessel 20. As another example, the exterior fluid passage 28 may be an enclosed lumen 28" that is substantially exterior to the vessel's walls 22. It will be appreciated that additional configurations and placement locations for the exterior fluid passage 28 can be contemplated by one of ordinary skill in the art.

Figure 3B:
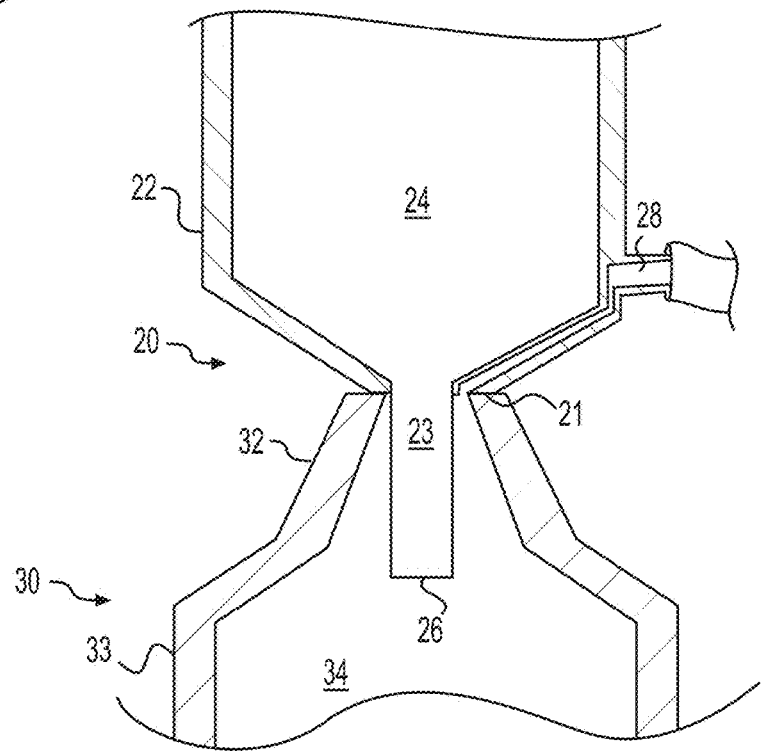
FIG. 3B illustrates a cross-sectional view of a portion of a system for transferring tissue, according to various embodiments.

Furthermore, other variations to the device 10 (including variations to the vessel 20 and/or syringe 30) can be made. For example, FIG. 3B shows an alternative embodiment of the material holding or processing vessel 20 wherein the ridge 25 is not present. Furthermore, in additional embodiments (not pictured), the ridge 25 can include other configurations, e.g., the ridge 25 may have straight or tapered walls. Further, the interior surface 27 of the ridge may be coated or covered with a material that is tacky or has non-slip properties, such as rubber, or may have a roughened surface to increase the frictional force that holds the syringe tip 32 in place.

Figure 4:
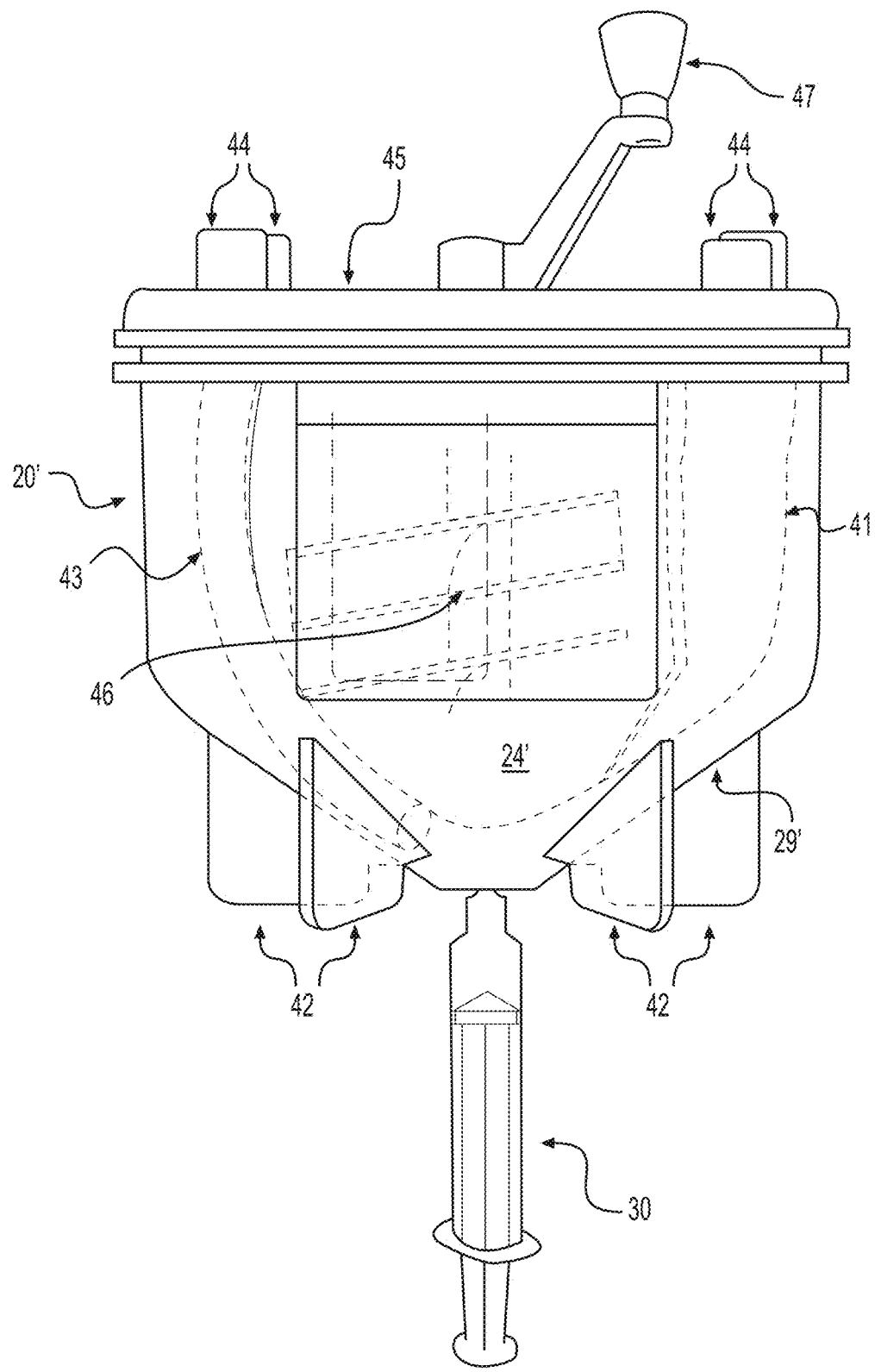
FIG. 4 illustrates a cross-sectional view of a system for processing and transferring tissue, according to various embodiments.

The devices disclosed herein can provide the ability to treat the tissue and then transfer the tissue directly into a syringe 30 without needing an additional transfer step and without opening the system 10. In some embodiments, the material holding or processing vessel 20' can additionally include elements to wash or treat tissue before the tissue is transmitted to the syringe 30' as shown in FIG. 4. Such elements include, but are not limited to, inlets and outlets for hoses or other tubes, filters, and mixing blades. For example, a vessel such as that provided with the REVOLVE™ system (LIFECELL CORPORATION, Branchburg, N.J.), which incorporates such features, may be adapted in accordance with the present disclosure. The present devices may be used with any tissue system wherein the tissue holding portion is open to atmospheric pressure to prevent negative pressure buildup with in the tissue holding portion during a transfer operation.

According to various embodiments, the material holding or processing vessel may include several support feet 42 to allow the device to rest on a table without tipping. The interior volume 24' of the vessel 20' may contain several additional components to facilitate tissue washing and processing. In various embodiments, the material holding or processing vessel 20' may contain a mesh filter 41 to support the tissue above the bottom portion 29' of the vessel prior to washing. The mesh filter 41 may be used to retain unwanted components of the tissue while allowing desirable cells and tissue components to pass through. In one embodiment, the mesh filter is a 100-500 micron filter that can capture collagen strands and stringy tissue. In accordance with various embodiments, one or more ports 44 may be present on a lid 45 of the material holding or processing device 20'. The ports 44 may be used as fluid inlets or fluid outlets to facilitate tissue washing and treatment. The ports 44 may be suitable to engage with catheter-tip or luer-lock syringe connectors or may be configured to connect to tubing using compression, barbed, luer, threaded, push-to-connect, flared, or any other suitable fittings meeting application-specific requirements. Based on this disclosure, one of ordinary skill in the art will appreciate that a port or ports 44 may be located in other places on the material holding or processing vessel 20' including, but not limited to, the lid 45, the exterior wall of the vessel 22', or the bottom portion of the vessel 29'.

In accordance with various embodiments, the interior volume 24' of the vessel 20' may contain a hose 43 to provide a direct connection between a port 44 on the lid 45 of the vessel and the portion of the interior volume 24' of the vessel 20' proximal to the bottom portion 29'. The hose 43 may be used to withdraw or insert fluids into the interior volume 24' of the vessel 20'. According to various embodiments, the interior volume 24' of the vessel 20' may also contain propelling or mixing blades 46 connected to a crank 47 on the lid 45 of the vessel 20. The crank 47 may be located in other places on the material holding or processing vessel 20' including, but not limited to, the lid 45, the exterior wall of the vessel 22', or the bottom portion of the vessel 29'.

By turning the mixing blades 46 with the crank 47, the tissue is actively mixed with cleaning solutions and physically processed. In some embodiments, the mixing blades 46 may include lower blades that scrape the bottom of the mesh filter 41 and lift up the tissue for thorough washing. In some embodiments, the mixing blades 46 may include a middle comb that sweeps the tissue and picks up stringy tissue and/or top blades that stir the tissue.

In some cases, it may be desirable to fill more than a single syringe at a time. For example, an operation may require more tissue than will fit in the volume of a single syringe, and to save time, it may be beneficial to allow simultaneous filling of multiple syringes. To address this need, the tissue transfer system may include a plurality of outlets and syringes to enable simultaneous or serial loading of multiple syringes at a time.

Figure 5:
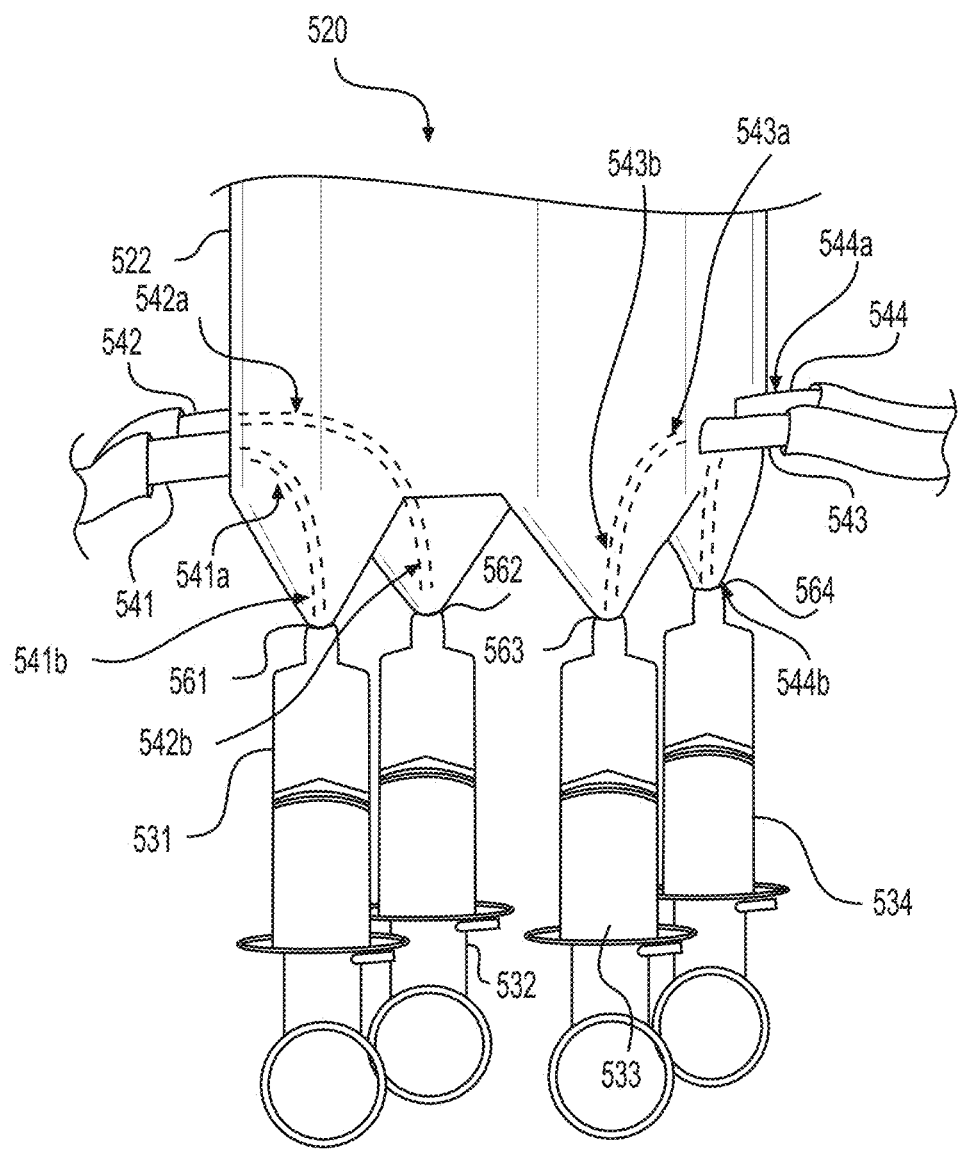
FIG. 5 illustrates a cross-sectional view of another system for tissue transfers, including components for transfer to multiple delivery devices simultaneously, according to various embodiments.

FIG. 5 illustrates an embodiment wherein the material holding or processing vessel 520 includes a plurality of outlets 561, 562, 563, 564 such that the vessel 520 can mate with a plurality of syringes 531, 532, 533, 534 simultaneously to transfer material. A plurality of plugs or valves may be provided to seal off outlets that are not needed or used in a particular transfer operation. The plugs or valves may be constructed of a variety of materials and may be permanently attached to the vessel or may be separate units. FIG. 5 depicts an exemplary embodiment that contains four outlets 561, 562, 563, 564 and four syringes 531, 532, 533, 534; however, it will be apparent in view of the present disclosure that any number of outlets and syringes can be used in accordance with various embodiments and that the number of outlets and syringes can vary depending upon application-specific requirements.

In one embodiment, the material holding or processing vessel 520 may include a plurality of discrete exterior fluid passages 541, 542, 543, 544 wherein the proximal end 541a, 542a, 543a, 544a of each passage is connected to an individual vessel outlet 561, 562, 563, 564, and the distal end 541b, 542b, 543b, 544b of each passage emerges separately from the vessel's exterior wall 522. In this embodiment, multiple negative pressure sources may be individually controlled to enable tissue transfer only into certain syringes chosen from a plurality of available syringes.

In another embodiment, the material holding or processing vessel 520 may include a single, multiply-connected exterior fluid passage with a plurality of proximal ends that are each connected to an individual vessel outlet 561, 562, 563, 564. Such an exterior fluid passage is advantageous if the number of available sources of negative pressure are limited or if the user desires to limit the number of external connections to the device. The plurality of proximal ends of the exterior fluid passage may be actuated individually using a set of valves to provide transfer tissue into only specific syringes chosen from among a plurality.

Figure 6:
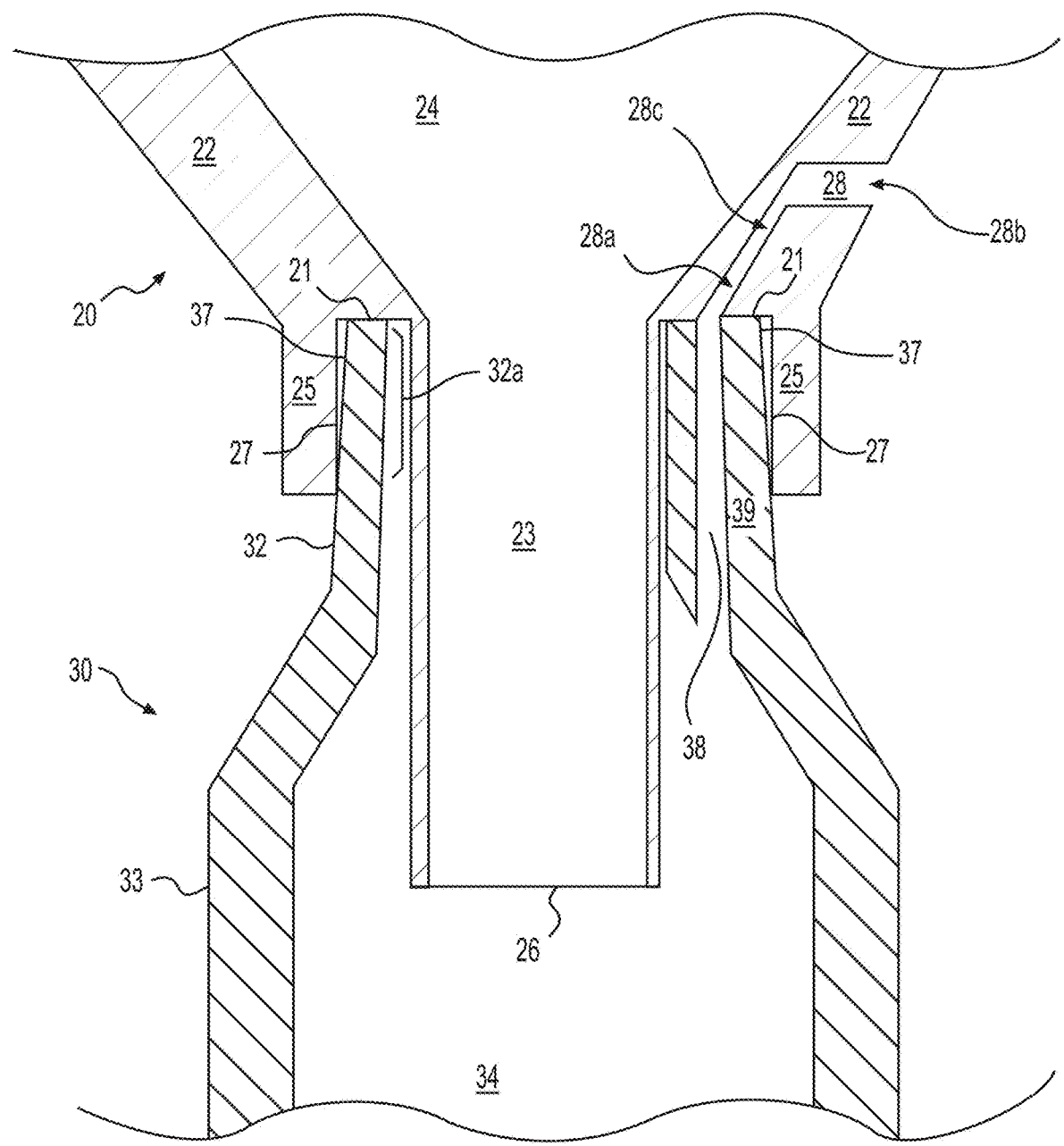
FIG. 6 illustrates a cross-sectional view of a portion of a system for transferring tissue wherein an external fluid passage of the vessel is in fluid communication with a secondary fluid passage in the peripheral wall of the syringe, according to various embodiments.

In certain embodiments, the syringe tip 32 may further include a second passage 38 through the peripheral wall 39 of the syringe 30 that is in fluid communication with the interior volume 34 of the syringe body 33 and the exterior fluid passage 28 of the vessel 20 as shown in FIG. 6. This second passage 38 can provide fluid communication between the distal end 28b of the exterior fluid passage 28 of the vessel 20, the interior volume 34 of the syringe 30 (through the peripheral wall 39), and the interior volume 24 of the vessel 20. When the syringe 30 is decoupled from the vessel 20, a plug can be introduced into the syringe's peripheral wall 39 to prevent material from escaping through the secondary passage 38 while the syringe is being used during re-implantation.

In another embodiment, a tissue transfer vessel is disclosed. The tissue transfer vessel may operate to transfer tissue into any container that can properly mate with the vessel's outlet.

Figure 7:
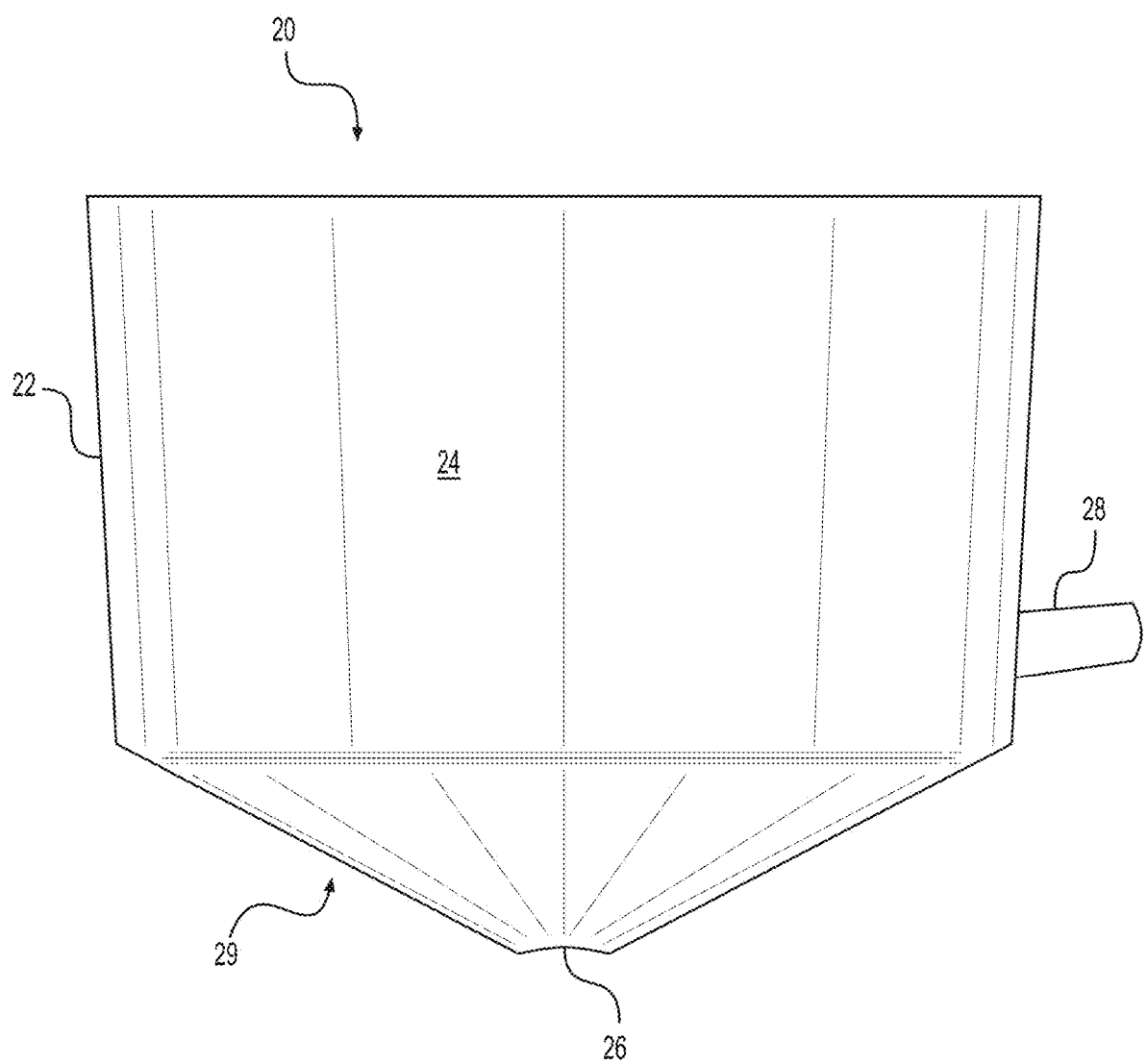
FIG. 7 illustrates a cross-sectional view of a portion of a device to fill syringes with tissue, according to various embodiments.

FIG. 7 illustrates a device to fill syringes with tissue, according to various embodiments. The device includes a material holding or processing vessel 20 that can further include an exterior wall 22 surrounding an interior volume 24 and an outlet 26 in fluid communication with the interior volume 24. The material holding or processing vessel 20 can also include an exterior fluid passage 28.

The material holding or processing vessel 20 can be formed of a variety of materials and have a variety of shapes. In some embodiments, the vessel 20 has a bottom portion 29 that is predominantly conical in nature and that terminates at an outlet 26. The outlet 26 can have a variety of suitable configurations, e.g., with a circular, elliptical, or other polygonal cross-sectional shape. In accordance with various embodiments, the material holding or processing vessel 20 can contain additional instruments to facilitate tissue washing or processing. These instruments may include, but are not limited to, mixing blades, fluid inlets, fluid outlets, and filters (see FIG. 4). According to various embodiments, the material holding or processing vessel 20 can have a plurality of outlets 26 and a plurality of exterior fluid passages 28. In some embodiments, the vessel 20 may have a plurality of discrete exterior fluid passages wherein the proximal end of each passage is connected to an individual vessel outlet and the distal end of each passage emerges separately from the vessel's exterior wall 22. In some embodiments, the vessel 20 may have a single, multiply-connected exterior fluid passage 28 with a plurality of proximal ends that are each connected to an individual vessel outlet.

In one embodiment, a tissue transfer system may include a tissue transfer adapter to facilitate transfer of a material out of a container or fluid conduit. As described in greater detail below, the tissue transfer adapter may include an adapter body having an outer wall and first, second, and third ends. In one embodiment, an elongated body containing a lumen may pass through the interior of the adapter body between the first end and the second end while a fluid passage passes through the interior of the adapter body between the third end and the second end. In some embodiments, an elongated body containing a lumen may pass through the interior of the adapter body between the third end and the second end while a fluid passage passes through the interior of the adapter body between the first end and the second end. Upon the application of suction to an opening in the third end, material contained within the container or fluid conduit is transferred through an opening in the first end to an opening in the second end through the adapter body. A tissue transfer adapter may be used with a variety of containers and adipose transfer devices.

Turning to FIG. 8A, a tissue transfer system 800 may include a material holding or processing vessel 820, an adapter 810, and a syringe 830. As discussed further below, the adapter may include an adapter body 811 having an outer wall and a plurality of ends 810a, 810b, 810c that may be adapted to connect to the material holding or processing vessel 820, the syringe 830, or a source of negative pressure. Each of the plurality of ends 810a, 810b, 810c can have an opening. In addition, the adapter 810 may contain an elongated body 819 having a lumen 813 that is in fluid communication with both the interior volume 824 of the vessel 820 and the interior volume 834 of the syringe 830. In exemplary embodiments, the tissue transfer system 800 can be operated in the orientation shown in FIG. 8A (i.e., vertical with the syringe pointing downward).

A fluid passage 818 may be contained within the adapter body and may surround an elongated body 819. In some embodiments, the outer diameter of the elongated body 819 is small enough to leave clearance within the fluid passage 818 for air to flow. In an example embodiment where the elongated body 819 and the fluid passage 818 have cylindrical cross-sections, the outer diameter of the elongated body 819 could be as much as 90% or even 95% of the inner diameter of the fluid passage 818 and still leave room for sufficient airflow. A distal end 818b of the fluid passage 818 may be connected to a source of negative pressure, while the proximal end 818a of the fluid passage 818 is in fluid communication with the interior volume 834 of the syringe 830. In accordance with various embodiments, the adapter may be configured to prevent material from passing from the interior volume 824 of a material holding or processing vessel 820 into the fluid passage 818 through a first end 810a of an adapter body 811. When the syringe 830 and vessel 820 are mated to the adapter body 811 and a negative pressure is applied at the distal end 818b of the external fluid passage 818, tissue contained within the vessel 820 will be pulled from the interior volume 824 of the vessel 820, through at least a portion of the lumen 813, and into the interior volume 834 of the syringe body 833. In an exemplary embodiment, the inner diameter of the lumen 813 can be as large as possible to allow passage of viscous fluids. For example, the inner diameter of the lumen 813 can be large enough to allow passage of particles or cell clusters ranging in size from 200 microns to 3 mm. In some embodiments, the inner diameter of the lumen 813 can be at least 1.4 mm, which is the inner diameter of a luer-lock tip.

The adapter 810 may be formed of a variety of materials and have a variety of shapes. The adapter 810 depicted in FIG. 8A is shown as a three-way adapter. However, it will be apparent in view of the present disclosure that the adapter 810 may include any number of ends and/or outlets in accordance with various embodiments and that the number of ends and/or outlets can vary depending upon application-specific requirements. The ends 810a, 810b, 810c of the adapter 810 may be tubular or have flat sides, and the individual ends may have any length as demanded by application-specific requirements. The ends 810a, 810b, 810c may terminate in any of a variety of connectors including luer-type connections, threaded fittings, tube fittings, straight-walled or bare tubes, or any other connection as required by a specific application.

In accordance with various embodiments, a fluid passage 818 and the lumen 813 of an elongated body 819 may not be in fluid communication with one another within the adapter body 811 but may be in fluid communication through an outlet 816 external to the adapter body 811. The distal end 813b of the lumen 813 contained within the elongated body 819 may be adapted to mate with the outlet 826 of the vessel 820 such that a leak-free seal is created between the vessel 820 and the lumen 813. The fluid passage 818 may include all of the remaining interior volume of the adapter body 811 that is not contained within the elongated body 819, or it may be characterized as a separate channel or lumen.

The elongated body 819 may be created of a variety of materials and may take a variety of shapes. For example, the elongated body 819 can be made of stainless steel, metals, plastics, or any other substance that is compatible with the material to be transferred and meets application-specific requirements. The elongated body 819 may contain a lumen 813 and can pass through the adapter body 811. The proximal end 813a of the lumen 813 contained within the elongated body 819 may terminate in an outlet 816 and may also extend out of the adapter 810 and into the mated syringe 830. In certain embodiments, the outlet 816 lies within the syringe body 833 and beyond the syringe tip 832. In accordance with various embodiments, an elongated body 819 may contain an exit port 815 located on a portion of the elongated body 819 exterior to the adapter body 811. In some embodiments, the outlet 816 or exit port 815 can be placed at least 3 mm gravitationally lower than the adapter body 811. In exemplary embodiments, the outlet 816 or exit port 815 can be placed below the neck of the syringe body 833 so that the transferred tissue will fall into the syringe without being carried up into the external fluid passage 818 by the passage of air. In embodiments that contain an exit port 815, the outlet 816 of the elongated body 819 may be closed or sealed shut. Further to such embodiments, the elongated body 819 can act as a syringe plunger depressor that prevents the syringe plunger 836 from entering the syringe body 834 while the syringe 830 is attached to the adapter body 811.

The material holding or processing vessel 820 can be formed of a variety of materials and have a variety of shapes. In some embodiments, the vessel 820 is a rigid structure having a bottom portion 829 that is predominantly conical in nature. The bottom portion 829 may terminate in an outlet 826. The outlet 826 may take any of a number of shapes or forms including, for example but not limited to, circular, elliptical, hexagonal, or polygonal shapes. According to various embodiments, the exterior wall 822 of the bottom portion 829 may include additional elements to allow coupling of the vessel 820 with various connectors. These elements may include, but are not limited to, luer fittings, pipe threads, tube fittings, or any other suitable fitting as required by a particular application.

The syringe 830 may include a plunger 836 that is adapted to move longitudinally within the syringe body 833. When the syringe 830 is mated to the adapter body 811, the plunger 836 seals the interior volume 834 of the syringe 830 to allow a negative pressure source connected to the distal end 818b of the fluid passage 818 of the adapter 810 to create negative pressure within the interior volume of the syringe 834. When the syringe 830 is unmated from the adapter 810, the plunger 836 can be used to force material out of the syringe's interior volume 834 through the syringe tip 832. According to various embodiments, the end 832a of the syringe tip 832 may include additional elements to allow coupling of the syringe 830 with various connector types. These elements may include, but are not limited to, luer fittings, pipe threads, tube fittings, or any other suitable fitting as required by a particular application.

With reference to FIG. 8B, an alternate embodiment of a tissue transfer system 805 may include a material transfer tube 860, an adapter 840, and a syringe 830. As discussed further below, the adapter may include an adapter body 841 having an outer wall and a plurality of ends 840a, 840b, 840c that are adapted to connect to the material transfer tube 860, the syringe 830, or a source of negative pressure. Each of the plurality of ends 840a, 840b, 840c can have an opening. In addition, the adapter 840 may contain a fluid passage 843 that is in fluid communication with the interior volume 864 of the transfer tube 860 and the interior volume 834 of the syringe 830. A distal end 848b of a lumen 848 contained within an elongated body 849 may be connected to a source of negative pressure while a proximal end 848a of the lumen 848 is in fluid communication with the interior volume 834 of the syringe. When the syringe 830 and tube 860 are mated to the adapter body 841 and a negative pressure is applied at the distal end 848b of the lumen 848, tissue material contained within the tube 860 will be pulled from the interior volume 864 of the tube 860, through the fluid passage 843, and into the interior volume 834 of the syringe body 833. In exemplary embodiments, the system 805 of FIG. 8B can be operated as close to vertical as possible as depicted in the figure.

The adapter 840 may be formed of a variety of materials and have a variety of shapes. The adapter 840 depicted in FIG. 8B is shown as a three-way adapter. However, it will be apparent in view of the present disclosure that the adapter 840 may have any number of ends and/or outlets in accordance with various embodiments and that the number of ends and/or outlets can vary depending upon application-specific requirements. The ends 840a, 840b, 840c of the adapter 840 may be tubular or have flat sides, and the individual ends may have any length as demanded by application-specific requirements. The ends 840a, 840b, 840c may terminate in any of a variety of connectors including luer-type connections, threaded fittings, tube fittings, straight-walled or bare tubes, or any other connection as required by a specific application.

In accordance with various embodiments, a lumen 848 contained within an elongated body 849 and a fluid passage 843 may not be in fluid communication with one another within the adapter body 841. The distal end 843b of the fluid passage 843 may be adapted to mate with the outlet 866 of the tube 860 such that a leak-free seal is created between the tube 860 and the fluid passage 843. The fluid passage 843 may include all of the remaining interior volume of the adapter body 841 that is not contained within the elongated body 849, or it may be characterized as a separate channel or lumen.

The elongated body 849 may be created of a variety of materials and may take a variety of shapes. For example, the elongated body 849 can be made of stainless steel, metals, plastics, or any other substance that is compatible with the material to be transferred and that meets application-specific requirements. The proximal end 848a of the lumen 848 may terminate in an outlet 846 and may also extend out of the adapter body 841 and into the mated syringe 830. In certain embodiments, the outlet 846 lies within the syringe body 833 and beyond the syringe tip 832. In accordance with various embodiments, the length of the elongated body 849 containing a lumen 848 is determined by the volume of tissue that is desired to be transferred into the syringe 830. Operation of the system beyond the pre-determined maximum transfer volume may cause tissue to be aspirated into the proximal end 848a of the lumen 848. In some embodiments, the elongated body 849 can contain an air inlet port 845. The air inlet port 845 can allow air to pass into the elongated body 849 even if the outlet 846 is blocked by contact with a portion of the syringe plunger 833.

The material transfer tube 860 can be separately formed or may be formed integrally with a material holding or processing vessel 20'. The tube 860 may be made from a variety of materials and may take the form of a variety of shapes and sizes. The tube 860 may be made of, for example but not limited to, PVC, high-density polyethylene, nylon, latex, silicone, polyurethane, TYGON®, or any other non-reactive tubing or hose as needed to meet application-specific requirements. The inner diameter, outer diameter, and wall thickness of the material transfer tube 860 may be any values suitable to meet application-specific requirements. In a preferred embodiment, the material transfer tube 860 extends from an exit point on the lid 45 of a material holding or processing vessel 20' to the bottom portion 29' of the vessel 20' where material is held before or after processing.

Figure 8C:
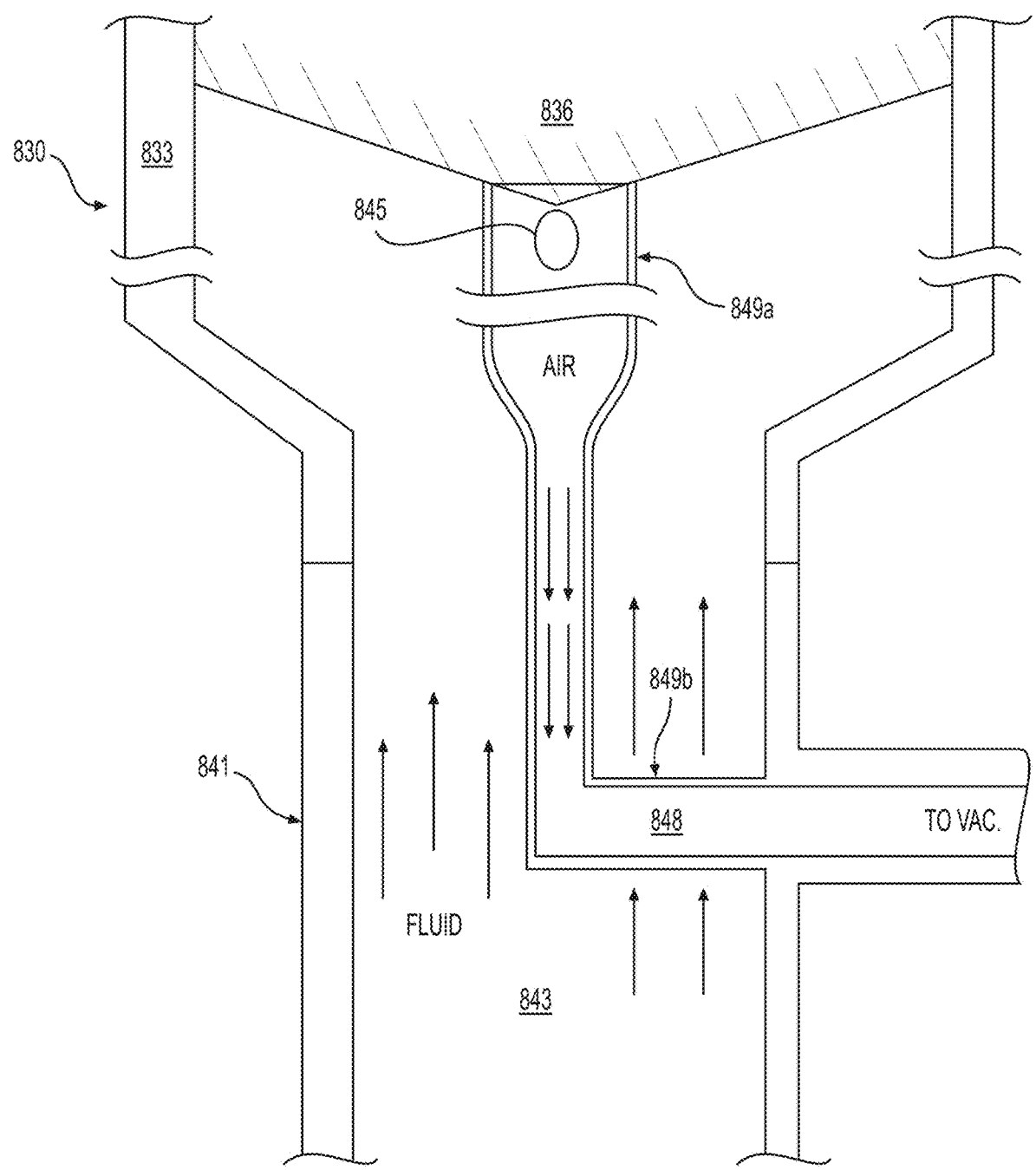
FIG. 8C illustrates an expanded view of an alternative embodiment of an elongated body shown in FIG. 8B according to various embodiments.

In FIG. 8C, an expanded view of an alternative embodiment of the elongated body 849 of FIG. 8B is depicted. As shown, the proximal end 849a and the distal end 849b of the elongated body 849 may have different outer diameters. In some embodiments, the outer diameter of the distal end 849b is minimized to create a maximized inner diameter of the fluid passage 843. A large inner diameter of the fluid passage 843 allows faster flow of viscous tissues or fluids into the syringe body 833. In certain embodiments, the outer diameter of the distal end 849b of the elongated body 849 is as small as 1 mm.

The outer diameter of the proximal end 849a of the elongated body can be flared in some embodiments to be larger than the outer diameter of the distal end 849b. Because the proximal end 849a of the elongated body 849 can act as a support column and physically block the syringe plunger 836 from entering the syringe body 833 during a transfer operation, a larger outer diameter can increase the buckling strength of the elongated body 849. In an exemplary embodiment, the outer diameter of the proximal end 849a of the elongated body 849 can be in a range of 3 to 4 mm. In some embodiments, the transition between the different outer diameters of the proximal end 849a and the distal end 849b can occur in the vicinity of the syringe tip 832.

Figure 8D:
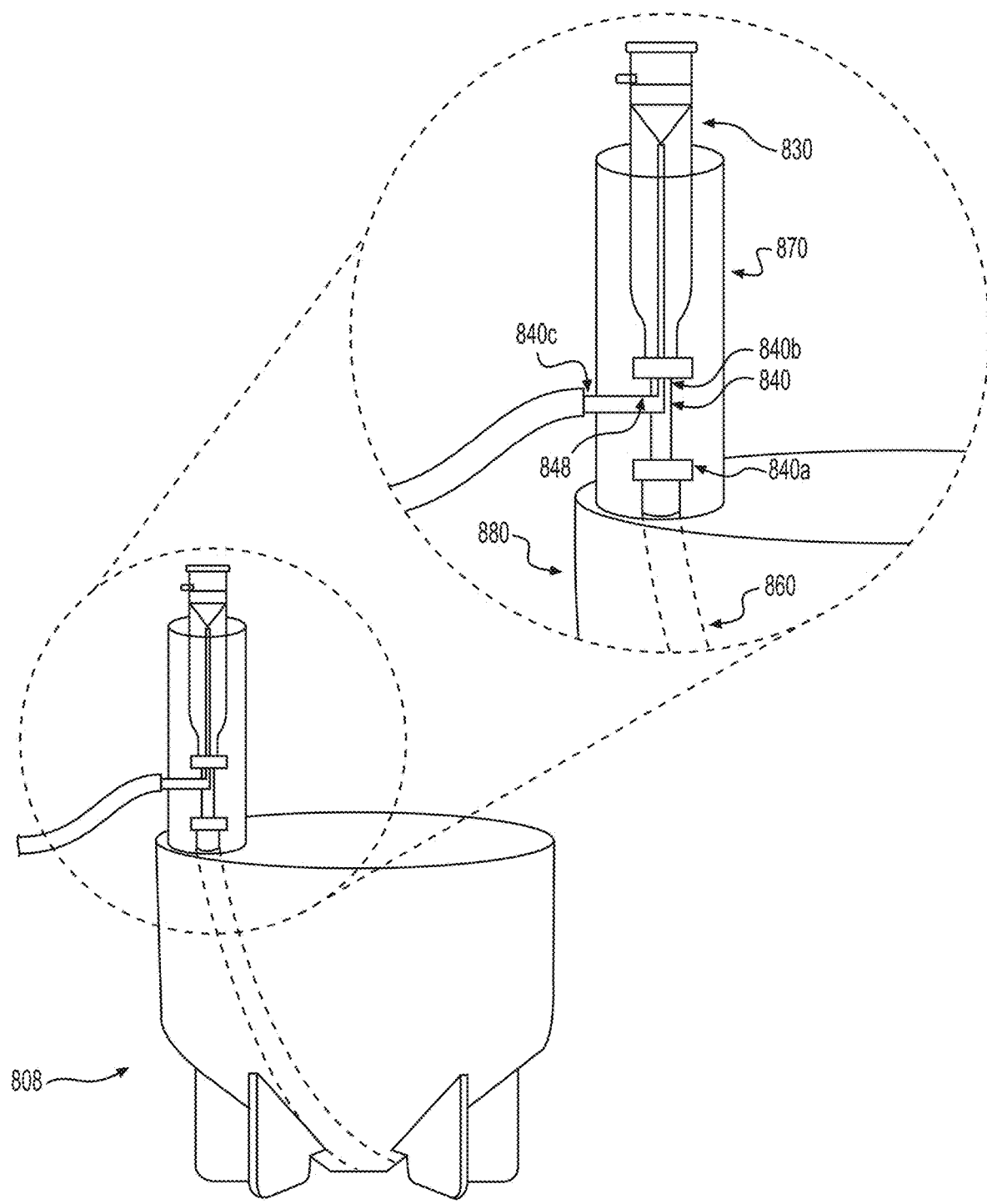
FIG. 8D illustrates an adapter of a tissue transfer system mounted to a material holding or processing vessel in accordance with various embodiments.

With reference to FIG. 8D, an adapter 840 of a tissue transfer system 808 may be mounted to a material holding or processing vessel 880. As discussed further below, the adapter 840 may include an adapter body 841 having a plurality of ends 840a, 840b, 840c that are adapted to connect to the material transfer tube 860, the syringe 830, or a source of negative pressure. Each of the plurality of ends 840a, 840b, 840c can have an opening. One or more of the plurality of ends 840a, 840b, 840c of the adapter 840 may be integrally constructed with the material holding or processing vessel 880 or may be adapted to connect to one or more ports on the vessel. One or more of the plurality of ends 840a, 840b, 840c may be in fluid communication with a material transfer tube 860. In accordance with various embodiments, the tissue transfer system 808 may include a protective sheath 870 that prevents a user from directly contacting the elongated body 849, which could potentially damage the elongated body 849 or injure the user.

The protective sheath 870 can be constructed of a variety of materials and may have a variety of shapes and sizes according to application-specific requirements. The protective sheath 870 may be made, for example but not limited to, metals or rigid plastics. The inner diameter of the protective sheath 870 may be chosen to accommodate the passage of a syringe 830. According to various embodiments, the protective sheath 870 may be attached to the material holding or processing vessel 880 or the adapter 840. In some embodiments, the protective sheath 870 may be detached from its mount and replaced with a sheath having similar properties or different properties including, but not limited to, inner diameter, size, or composition.

Figure 8E:
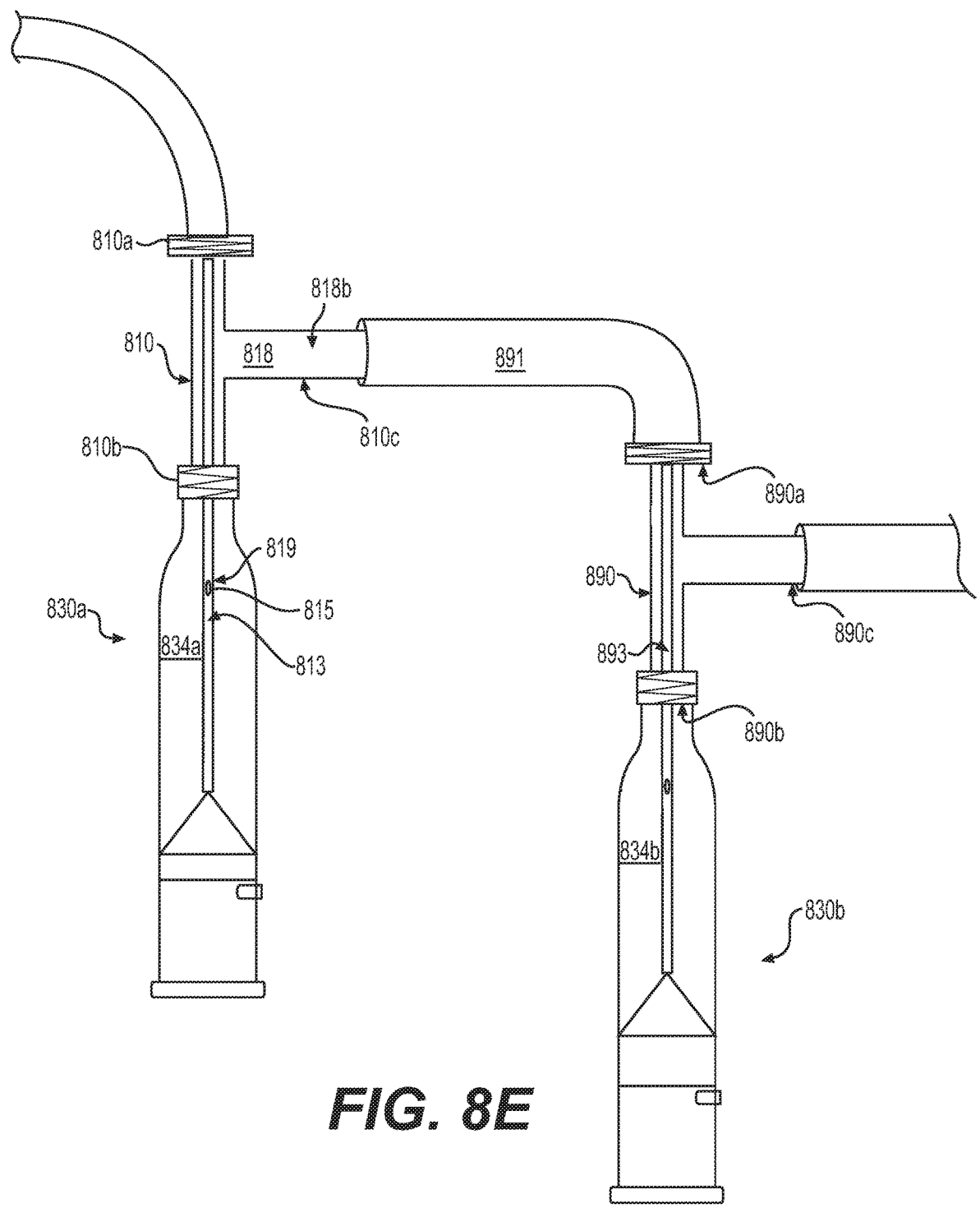
FIG. 8E illustrates adapters of a tissue transfer system connected in series in accordance with various embodiments.

With reference to FIG. 8E, multiple syringes 830a, 830b may be filled in sequence by connecting two or more adapters 810, 890 in series. A source of negative pressure may be applied to an end 890c of the final adapter 890. The negative pressure can thereby be communicated through all of the adapters 810, 890 and interiors 834a, 834b of syringes 830a, 830b before reaching a material holding or processing vessel 820 or material transfer tube 860 containing tissue to be transferred. The negative pressure can draw the tissue into a lumen 813 of a first adapter 810. When the tissue reaches an exit port 815 of the lumen 813, the tissue exits the lumen 813 and begins to fill the interior volume 834a of the first syringe 830a. When the interior volume 834a of the first syringe 830a is filled, the tissue can continue to fill into the fluid passage 818 of the first adapter 810. The tissue can then be pulled through a transfer tube 891 and can enter a lumen 893 of a second adapter 890. When all of the syringes 830a, 830b have become full, the negative pressure source may be shut off to prevent clogging. For clarity, only two adapters and two syringes are displayed in FIG. 8E; however, it will be apparent from this disclosure to one skilled in the art that an unlimited number of adapters and syringes could potentially be used in series as described herein. In an alternative embodiment, a plurality of syringes 830a, 830b can be connected to a vacuum manifold in parallel rather than in series to reduce the path the tissue must travel to reach the final syringe in series.

The process and method of safely transferring tissue in an automated way is also illuminated in this manuscript. In an exemplary method, a system similar to that described above is engaged with a source of negative pressure to transfer the tissue from a vessel to a syringe.

Figure 9:
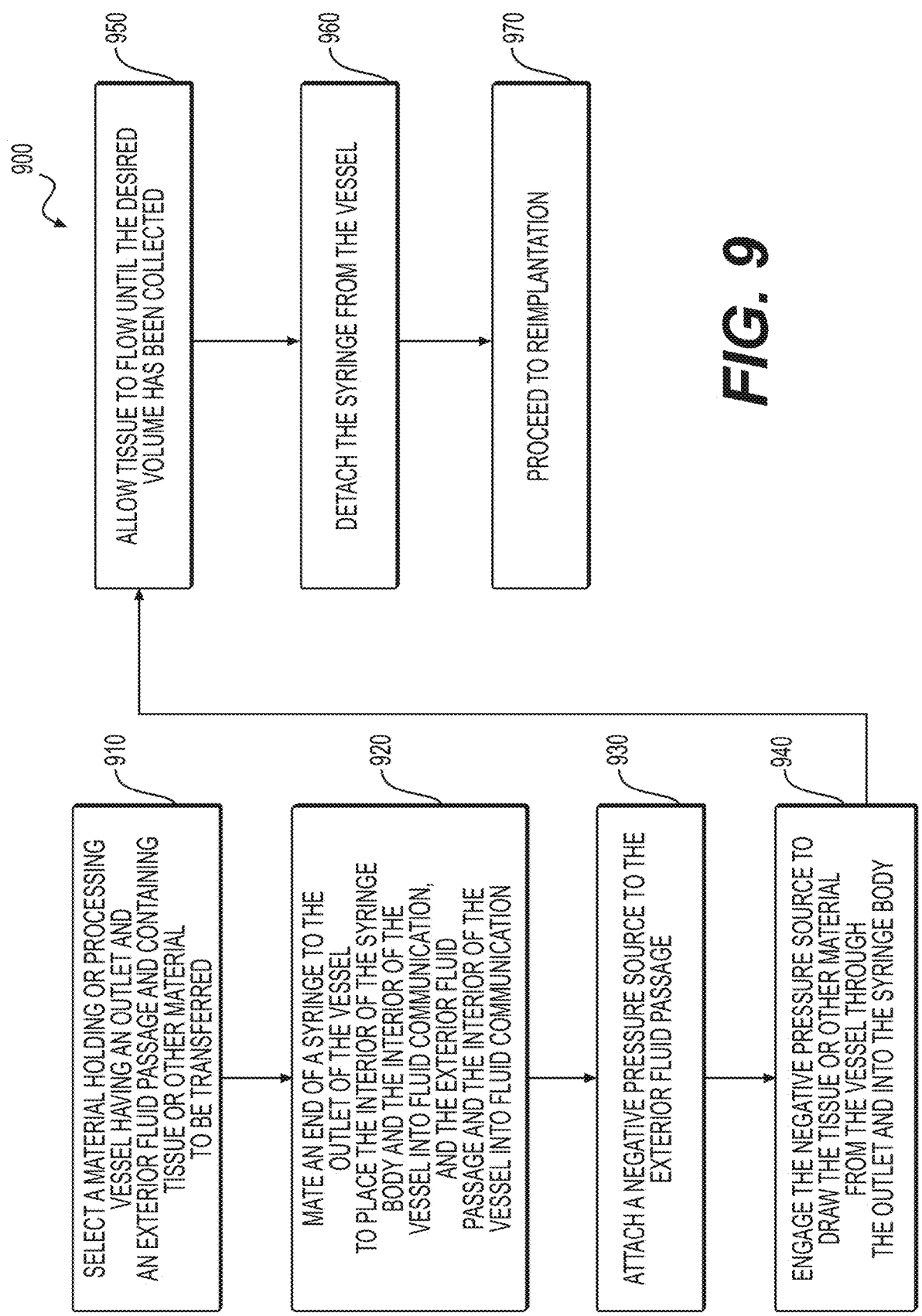
FIG. 9 is a flow chart illustrating steps of a method for tissue transfer, according to various embodiments.

FIG. 9 illustrates an exemplary method 900 for tissue transfer. The method 900 includes selecting 910 a material holding or processing vessel having an outlet and an exterior fluid passage and containing tissue or other material to be transferred. The method 900 includes mating 920 an end of a syringe to the outlet of the vessel to place the interior of the syringe body and the interior of the vessel into fluid communication, and the exterior fluid passage and the interior of the vessel into fluid communication. The method 900 includes attaching 930 a negative pressure source to the exterior fluid passage. The method 900 includes engaging 940 the negative pressure source to draw the tissue or other material from the vessel through the outlet and into the syringe body. The method 900 includes allowing 950 tissue to flow until the desired volume has been collected. The method 900 includes detaching 960 the syringe from the vessel. The method 900 includes proceeding 970 to re-implantation.

The step of selecting 910 a material holding or processing vessel having an outlet and an exterior fluid passage and containing tissue or other material to be transferred can include, for example but not limited to, selecting a material holding or processing vessel 20 including an outlet 26 and an exterior fluid passage 28 and filled with adipose tissue as described above in connection with FIGS. 1A, 1B, and 2.

The step of mating 920 an end of a syringe to the outlet of the vessel to place the interior of the syringe body and the interior of the vessel into fluid communication, and the exterior fluid passage and the interior of the vessel into fluid communication can include, for example but not limited to, coupling an end 32a of a syringe 30 to an outlet 26 of a vessel 20 such that the interior surface 27 of a ridge 25 is in contact with the peripheral wall 39 of the syringe 30 as described above in connection with FIGS. 1A, 1B, and 2.

The step of attaching 930 a negative pressure source to the exterior fluid passage can include, for example but not limited to, attaching a standalone vacuum pump or in-house vacuum provided in an operating room or related facility as described above in connection with FIGS. 1A, 1B, and 2.

The step of engaging 940 the negative pressure source to draw the tissue or other material from the vessel through the outlet and into the syringe body can include, for example but not limited to, powering on a vacuum pump or releasing a hose clamp to enable the vacuum source to draw tissue from a vessel 20 through an outlet 26 and into a syringe body 33 as described above in connection with FIGS. 1A, 1B, and 2.

The step of allowing 950 tissue to flow until the desired volume has been collected can include, for example but not limited to, determining how much tissue is available to be transferred and/or how much tissue is needed in the new location and using that determination to disable the vacuum source when the proper volume has been reached.

The step of detaching 960 the syringe from the vessel can include, for example but not limited to, disconnecting the syringe 30 from the vessel 20 as described above in connection with FIGS. 1A, 1B, and 2.

The step of proceeding 970 to re-implantation can include, for example but not limited to, attaching a needle or cannula to a syringe tip 32 of a syringe 30, releasing a plunger lock 37 on the syringe 30, and injecting tissue into a patient.

Other embodiments will be apparent to those skilled in the art from consideration of the specification and practice of this disclosure. It is intended that the specification and examples be considered as exemplary only, with the true scope and spirit of the disclosed devices and methods being indicated by the following claims.

What is claimed is:

1. A tissue transfer system, comprising:
  a material holding or processing vessel, including:
    an exterior wall surrounding an interior vessel volume for holding tissue;
    an outlet in fluid communication with the interior vessel volume; and
    an exterior fluid passage having an opening disposed proximate an opening of the outlet;
  a syringe, including:
    a syringe body having an interior syringe volume; and
    a syringe tip comprising a peripheral wall having a distal opening forming a first passage in fluid communication with the interior vessel volume, wherein the syringe tip is adapted to be mated with the outlet of the material holding or processing vessel such that the opening of the outlet is in fluid communication with the first passage of the syringe tip and the exterior fluid passage of the material holding or processing vessel is in fluid communication with the interior syringe volume of the syringe body; and
  wherein application of negative pressure at the exterior fluid passage draws tissue through the outlet and into the interior syringe volume.

2. The system of claim 1, wherein the material holding or processing vessel further comprises an elongated lumen extending from the exterior wall to the outlet.

3. The system of claim 1, wherein the material holding or processing vessel further comprises a ridge whose interior surface is configured to mate with an exterior lateral surface of the syringe tip.

4. The system of claim 1, wherein the material holding or processing vessel comprises a mating surface that connects with an end of the syringe tip.

5. The system of claim 1, wherein a distal end of the exterior fluid passage comprises an adapter to facilitate connection to a source of negative pressure.

6. The system of claim 1, wherein the syringe further comprises a plunger adapted to move longitudinally within the syringe body.

7. The system of claim 6, wherein the syringe further comprises a locking mechanism for securing the plunger in a selected longitudinal position.

8. The system of claim 1, wherein the exterior fluid passage has a proximal opening, a lumen, and a distal opening, wherein the proximal opening, lumen, and distal opening are external to the interior vessel volume, and the distal opening is located proximate an opening of the outlet.

9. The system of claim 1, wherein the material holding or processing vessel further comprises at least one mixing blade, filter, fluid inlet, or fluid outlet to facilitate tissue washing or treatment.

10. The system of claim 1, wherein the vessel comprises a plurality of outlets and a plurality of exterior fluid passages to allow the vessel to mate with multiple syringes.

11. The system of claim 1, wherein the syringe tip further comprises a second passage through the peripheral wall in fluid communication with the interior syringe volume of the syringe body and the exterior fluid passage of the vessel.

12. A tissue transfer vessel, comprising:
   an exterior wall surrounding an interior volume for holding a tissue;
   an elongated lumen extending from the exterior wall to an outlet;
   an exterior fluid passage having a proximal opening, a lumen, and a distal opening, wherein the proximal opening, lumen, and distal opening are external to the interior volume, and the distal opening is located proximate an opening of the outlet, the lumen of the exterior fluid passage at least partly embedded within the exterior wall; and
   a ridge surrounding the elongated lumen whose interior surface is configured to mate with an exterior lateral surface of a syringe tip.

13. The vessel of claim 12, wherein a portion of the exterior wall surrounding the elongated lumen outlet comprises a mating surface that connects with an end of a syringe tip.

14. The vessel of claim 12, wherein the tissue transfer vessel further comprises at least one mixing blade, filter, fluid inlet, or fluid outlet to facilitate tissue washing or treatment.

* * * * *